(12) United States Patent
Shumate et al.

(10) Patent No.: US 6,372,185 B1
(45) Date of Patent: Apr. 16, 2002

(54) LIQUID CHEMICAL DISTRIBUTION METHOD AND APPARATUS

(75) Inventors: Christopher Bentley Shumate, San Francisco; Peter J. Coassin, Encinitas, both of CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/228,258

(22) Filed: Jan. 11, 1999

Related U.S. Application Data

(63) Continuation-in-part of application No. 08/858,016, filed on May 16, 1997, now Pat. No. 5,985,214.

(51) Int. Cl.7 .................................................. B01L 3/02
(52) U.S. Cl. ........................ 422/100; 422/63; 422/99; 422/104; 436/43; 436/47; 436/174; 436/180
(58) Field of Search ....................... 422/99–104, 62–65; 436/43, 47, 174, 179, 180; 73/863, 863.01, 863.31, 863.32, 863.33, 864, 864.01

(56) References Cited

U.S. PATENT DOCUMENTS

| | | | |
|---|---|---|---|
| 4,000,976 A | | 1/1977 | Kramer et al. |
| 4,058,146 A | | 11/1977 | Citrin |
| 4,115,010 A | | 9/1978 | McAleer et al. |
| 4,125,680 A | | 11/1978 | Shropshire et al. |
| 4,135,561 A | | 1/1979 | Senelonge |
| 4,216,245 A | * | 8/1980 | Johnson |
| 4,256,153 A | | 3/1981 | Lamaziere |
| 4,262,711 A | | 4/1981 | Anderson |

(List continued on next page.)

FOREIGN PATENT DOCUMENTS

| | | | |
|---|---|---|---|
| EP | 301699 | * | 1/1989 |
| EP | 0 251 441 B1 | | 12/1993 |
| EP | 0 635 713 A1 | | 1/1995 |
| WO | WO 88/00707 | | 1/1988 |
| WO | WO 91/04193 | | 4/1991 |
| WO | WO 91/16977 | | 11/1991 |
| WO | WO 91/17445 | | 11/1991 |
| WO | WO 92/14127 | | 8/1992 |
| WO | WO 93/13423 | | 7/1993 |

(List continued on next page.)

OTHER PUBLICATIONS

France, et al., Proceedings of the international Symposium on Laboratory Automation and Robotics, 1992, pp. 400–410.

Goddard, et al., Proceedings of the International Symposium on Laboratory Automation and Robotics. 1992. pp. 392–399.

Schroeder and Neagle, J. Biomolecular Screening, 1:75–80 (1996).

Ultra High Throughout Screening System, Zymark Corp. Home page down load. AlegroO Jul. 17, 1998.*

Primary Examiner—Jill Warden
Assistant Examiner—Dwayne K. Handy
(74) Attorney, Agent, or Firm—Knobbe, Martens, Olson & Bear, LLP.

(57) ABSTRACT

A chemical solution distribution system and method that includes or employs a plurality of liquid handlers where each of the liquid handlers includes a movable table that engages a sample multiwell plate and can align pipettes of the station with different subsets of wells of the multiwell plate where the number of wells of the multiwell plate is a multiple of the number of pipettes of the head of the pipette station. The system further includes and employs four different pumps to enable the system and method to supply four different solutions to wash stations of each of the four liquid handlers.

30 Claims, 7 Drawing Sheets

U.S. PATENT DOCUMENTS

| | | |
|---|---|---|
| 4,276,048 A | 6/1981 | Leaback |
| 4,313,476 A | 2/1982 | Bennett et al. |
| 4,342,407 A | 8/1982 | Citrin |
| 4,446,104 A | 5/1984 | Hammerling et al. |
| 4,478,094 A | 10/1984 | Salomaa et al. |
| 4,488,241 A | 12/1984 | Hutchins et al. |
| 4,493,896 A | 1/1985 | La Motte, III et al. |
| 4,496,657 A | 1/1985 | Coppersmith et al. |
| 4,498,782 A | 2/1985 | Proctor et al. |
| 4,501,970 A | 2/1985 | Nelson |
| 4,507,044 A | 3/1985 | Hutchins et al. |
| 4,510,684 A | 4/1985 | Hutchins et al. |
| 4,562,871 A | 1/1986 | Astle |
| 4,565,100 A | 1/1986 | Malinoff |
| 4,580,895 A | 4/1986 | Patel |
| 4,586,151 A | 4/1986 | Boute |
| 4,607,196 A | 8/1986 | Abrahams et al. |
| 4,632,631 A | 12/1986 | Dunlap |
| RE32,414 E | 5/1987 | Hutchins et al. |
| 4,677,195 A | 6/1987 | Hewick et al. |
| 4,692,308 A | 9/1987 | Riley et al. |
| 4,701,412 A | 10/1987 | Naylor |
| 4,701,754 A | 10/1987 | Provonchee |
| 4,703,008 A | 10/1987 | Lin |
| 4,710,031 A | 12/1987 | Kelly et al. |
| 4,753,775 A | 6/1988 | Ebersole et al. |
| 4,803,050 A | 2/1989 | Mack |
| 4,824,230 A | 4/1989 | Litt |
| 4,835,711 A | 5/1989 | Hutchins et al. |
| 4,968,148 A | 11/1990 | Chow et al. |
| 5,021,217 A | 6/1991 | Oshikubo |
| 5,035,270 A | 7/1991 | Herzog |
| 5,036,001 A * | 7/1991 | Gork et al. |
| 5,055,263 A | 10/1991 | Meltzer |
| 5,073,029 A | 12/1991 | Eberly et al. |
| 5,082,628 A * | 1/1992 | Andreotti et al. |
| 5,104,621 A * | 4/1992 | Pfost et al. |
| 5,104,808 A | 4/1992 | Laska et al. |
| 5,108,703 A | 4/1992 | Pfost et al. |
| 5,112,134 A | 5/1992 | Chow et al. |
| 5,125,748 A | 6/1992 | Bjornson et al. |
| 5,139,744 A | 8/1992 | Kowalski |
| 5,206,568 A | 4/1993 | Bjornson et al. |
| 5,213,766 A | 5/1993 | Flesher et al. |
| 5,219,528 A | 6/1993 | Clark |
| 5,226,462 A | 7/1993 | Carl |
| 5,243,540 A | 9/1993 | Van Albert et al. |
| 5,250,263 A | 10/1993 | Manz |
| 5,332,549 A | 7/1994 | MacIndoe, Jr. |
| 5,338,688 A * | 8/1994 | Deeg et al. |
| 5,350,564 A | 9/1994 | Mazza et al. |
| 5,355,215 A | 10/1994 | Schroeder et al. |
| 5,355,439 A | 10/1994 | Bernstein et al. |
| 5,362,648 A * | 11/1994 | Koreyasu et al. |
| 5,366,896 A | 11/1994 | Margrey et al. |
| 5,443,791 A * | 8/1995 | Cathcart et al. |
| 5,455,008 A | 10/1995 | Earley et al. |
| 5,468,110 A | 11/1995 | McDonald et al. |
| 5,497,670 A | 3/1996 | Carl |
| 5,512,247 A | 4/1996 | Bonacina et al. |
| 5,518,688 A | 5/1996 | Gianino |
| 5,525,302 A | 6/1996 | Astle |
| 5,527,684 A | 6/1996 | Mabile et al. |
| 5,540,889 A | 7/1996 | Gordon et al. |
| 5,542,012 A | 7/1996 | Fernandes et al. |
| 5,544,535 A | 8/1996 | Thomas |
| 5,547,849 A | 8/1996 | Baer et al. |
| 5,567,294 A | 10/1996 | Dovichi et al. |
| 5,578,832 A | 11/1996 | Trulson et al. |
| 5,580,722 A | 12/1996 | Foulkes et al. |
| 5,581,691 A | 12/1996 | Hsu et al. |
| 5,581,758 A | 12/1996 | Burnett et al. |
| 5,589,351 A | 12/1996 | Harootunian |
| 5,593,267 A | 1/1997 | McDonald et al. |
| 5,623,415 A * | 4/1997 | O'Bryan et al. |
| 5,665,543 A | 9/1997 | Foulkes et al. |
| 5,670,113 A | 9/1997 | Akong et al. |
| 5,675,715 A | 10/1997 | Bernstein et al. |
| 5,691,188 A | 11/1997 | Pausch et al. |
| 5,696,887 A | 12/1997 | Bernstein et al. |
| 5,776,502 A | 7/1998 | Foulkes et al. |
| 6,045,755 A * | 4/2000 | Lebl et al. .................... 422/65 |

FOREIGN PATENT DOCUMENTS

| | | |
|---|---|---|
| WO | WO 93/25913 | 12/1993 |
| WO | WO 95/11461 | 4/1995 |
| WO | WO 95/25423 | 9/1995 |
| WO | WO 95 31284 | 11/1995 |
| WO | WO 96/05488 | 2/1996 |
| WO | WO 97/00136 * | 1/1997 |
| WO | WO 97/26539 | 7/1997 |
| WO | WO 98/52047 * | 11/1998 |

* cited by examiner

Dispensing into 96 well plate, 6.5 mm diam. wells

Dispensing into 384 well plate, 3.4 mm diam. wells

Dispensing into 864 well plate, 2 mm diam. wells

LIQUID CHEMICAL DISTRIBUTION METHOD AND APPARATUS

CROSS REFERENCE TO RELATED APPLICATIONS

This application claims the benefit of an earlier filing date under 35 U.S.C., Section 120 to a patent application identified as Ser. No. 08/858,016, filed May 16, 1997, now U.S. Pat. No. 5,985,214 entitled, Systems and Methods for Rapidly Identifying Useful Chemicals in Liquid Samples by Stylli et al., of which the present application is a continuation in part.

TECHNICAL FIELD

The present invention generally relates to automated systems and methods for processing chemicals dissolved in solvents and for rapidly identifying chemicals with biological or toxic activity in liquid samples, particularly automated methods of reformating samples and the aspiration and dispensation of potential new medicines, agrochemicals, and cosmetics.

BACKGROUND

Systems and methods for rapidly identifying chemicals with biological or toxic activity in samples, especially small liquid samples, can benefit a number of different fields. For instance, the agrochemical, pharmaceutical, and medical diagnostics fields all have applications where large numbers of liquid samples containing chemicals are processed. Currently, many such fields use various strategies to reduce processing times, such as simplified chemistry, semi-automation and robotics. While such strategies may improve the processing time for a particular single type of liquid sample, process step or chemical reaction, such methods or apparatuses can seldom efficiently process many thousands of dissimilar samples, for example as found in a chemical library, or in a nucleic acid array. As the size of chemical libraries and nucleic acid arrays has grown, the rate at which complex libraries can be accurately distributed for testing or analysis has become rate-limiting. In particular, there is a need to develop methods and devices that can rapidly process many thousands of different samples and accurately and reproducibly distribute or redistribute known amounts of those samples for further analysis. Central to this need is a requirement to efficiently handle a multitude of different liquid samples, such as chemical or nucleic acid libraries present in chemical or sample multiwell plates of varying densities and formats.

Multiwell plates may be orientated and configured in a variety of designs and formats and be present either with, or without, lids. For example, multiwell plates, commonly known as "microplates", have been in common use for decades with a predominant format being a molded plastic multiwell plate having 96 sample wells in an 8×12 rectangular array. Typical well volumes are 200 or 300 microliters, depending upon the manufacturer and model of multiwell plate, although other volumes may be provided for specific uses, for example see Whatman/Polyfiltronics 1998 Microplate Product Guide. Polyfiltronics Inc., 136 Weymouth Street, Rockland, Mass. 02370 USA. A proposed standard, designated "Microplate 96-Well Standard" (MP96) has been promulgated by The Society for Biomolecular Screening, as published in Journal of Biomolecular Screening, Volume 1, Number 4, 1996, the disclosure of which is incorporated herein by reference. A multiwell plate which meets the general dimensional requirements of the standard is designated MP96-3. Typically, each multiwell plate manufacturer will also provide a compatible lid. A typical lid comprises a generally rectangular flat planar top surrounded by a flange depending from the top along its sides and edges.

Multiwell plates are used for many different types of applications, including chemical library generation and storage, additionally multiwell plates may also be used to hold arrays of polynucleotides for use in expression analysis, or genomic analysis, as described in for example, Schena (1996) Genome analysis with gene expression microarrays BioEssays 18 no 5 427–431; Johnson (1998), Gene chips: Array of hope for understanding gene regulation Current Biology 8 R171–R174; Scholler et al. (1998) Optimization and automation of fluorescence-based DNA hybridization for high-throughput clone mapping Electrophoresis 19 504–508. Multiwell plates may also be used for gene amplification using the polymerase chain reaction as described in U.S. Pat. No. 5,545,528 entitled Rapid Screening Method of Gene Amplification Products in Polypropylene Plates.

The advent of high throughput analysis and increasing use of miniaturized formats has also lead to the development of higher format multiwell plates for example, 384, 864 and 3456 wells as described in PCT patent application identified by serial number PCT/US98/11061 entitled Low Background Multi-Well Plates With Greater Than 864 Wells for Fluorescence Measurements of Biological and Biochemical Samples, published Dec. 2, 1998. Even higher density sample processing systems, for example using chips that contain miniaturized microfluidic devices are being developed (see for example, Marshall (1998) Lab-on-a Chip: Biotech's Next California Gold Rush R & D Magazine, November 1998, pages 38 to 43).

Higher density multiwell plates enable faster analysis and handling of large sample or chemical libraries, such as in automated screening systems. However, irrespective of the final plate density, the inventors have often recognized that the overall throughput of the system is limited by the requirement to distribute chemical solutions from multiwell plates with a first well density to a second well density, particularly when the second well density is greater than 96 wells per plate. The need thus exists for a chemical solution distribution system that can rapidly and accurately process liquid samples on multiwell plates of different densities, particularly those with densities of greater than 96 wells per plate.

SUMMARY

Figure 1:
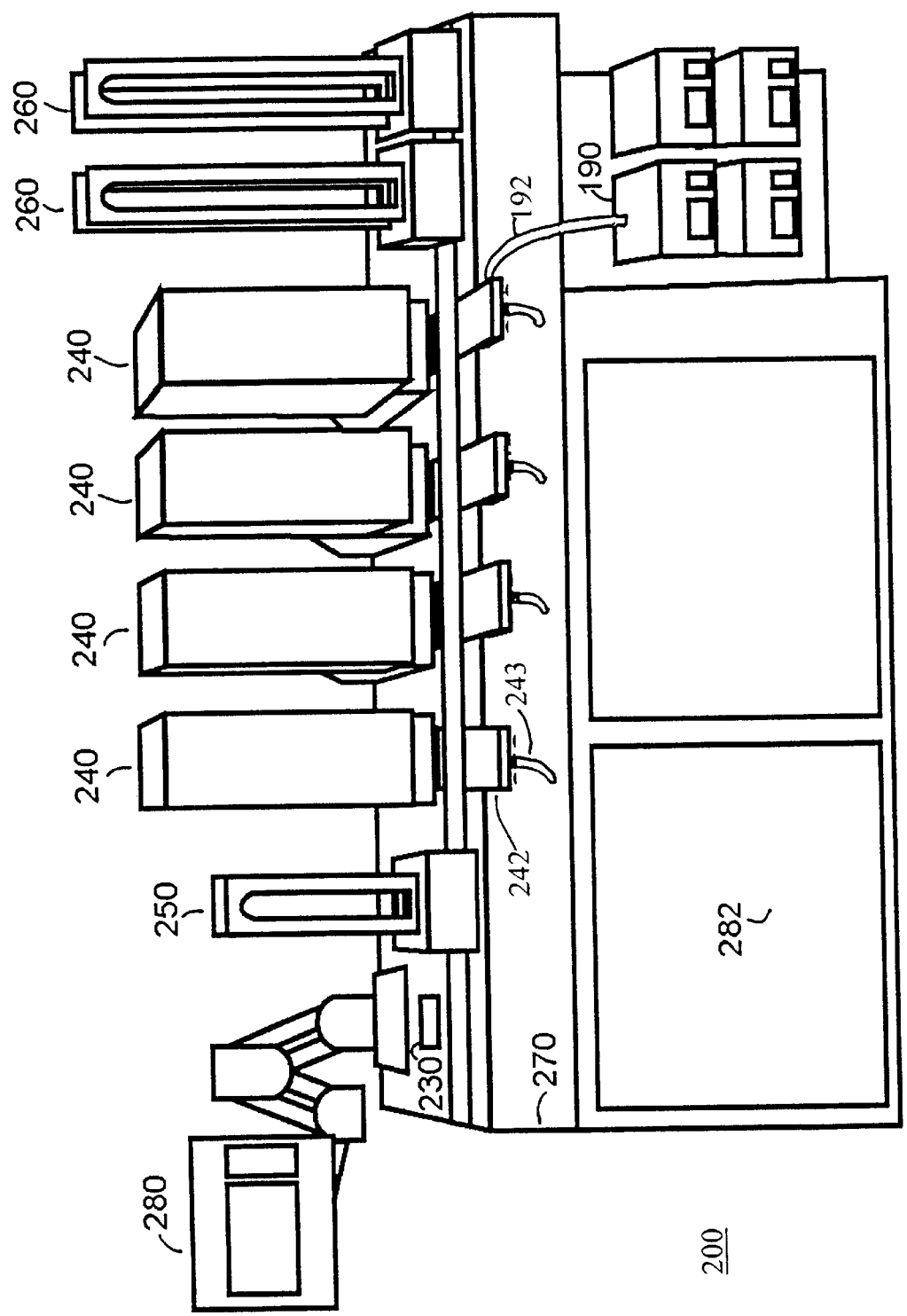
FIG. 1 is a diagram of an embodiment of a chemical solution distribution system according to the present invention.

In one embodiment, the invention is a chemical solution distribution system capable of rapidly distributing liquid samples between a plurality of multiwell plates including a first multiwell plate having a different number of wells from a second multiwell plate. The second plate having a number of wells greater than the number of the pipettes in a head of a liquid handler, typically in a defined pre-set matrix of immobile pipettes. In particular, one embodiment is directed to multiwell plates having a number of wells that are a multiple of the number of pipettes in a head of a liquid handler. The system typically distributes samples between a plurality of multiwell plates having N wells where the number of pipettes in a liquid handler is M. M is an integer multiple, I of N. Each of the plurality of multiwell plates is thus comprised of I subsets of M wells, N total (M*I wells). In this embodiment, the system includes a plurality of liquid handlers to enable parallel processing of multiwell plates. Each liquid handler includes a head movable in a Z-direction with M pipettes and a table configured to engage one of the plurality of multiwell plates and move in an X-Y plane relative to Z. Typically, the table is movable to at least I different positions. In each of the I positions, typically a different subset of M wells of the multiwell plates are aligned with the M pipettes of the head of the station. Such a chemical solution distribution system is suited for rapidly distributing samples of chemicals where the multiwell plates are chemical libraries or master multiwell plates. Also, in a preferred embodiment the system has I liquid handlers corresponding to the I subsets of M wells of each of the plurality of multiwell plates. In this embodiment, each liquid handler further includes a wash station below the head. In each station, typically the head is able to move the M pipettes in the Z-direction into contact with solution in the wash station. In addition, the system may include a different wash station solution pump for each liquid handler. Each pump is capable of delivering or providing a different solution to the wash station of each liquid handler. In order to improve the efficiency of the distribution system, the system may further include at least one multiwell plate stacker or buffer. The stacker is capable of storing a plurality of multiwell plates and enables adaptive routing of multiwell plates from the chemical solution distribution system to other system modules. In order to transfer a multiwell plate from the multiwell plate stacker to a liquid handler, the system may further include a multilane conveying system to enable parallel adaptive processing of multiwell plates. In some embodiments, the multiwell plates may have lids. In such a case, the system may further include a delidder capable or removing and replacing lids on plates. Typically, the multilane conveying system also communicates multiwell plates to a delidder.

In one exemplary embodiment, the system separately processes multiwell liquids in plates having 96 wells into plates with 384 wells, N equal to 384, and having 96 pipette heads in each liquid handler, M equal to 96 while maintaining the integrity, or discrete nature, of each solution. In this embodiment, there are typically four liquid handlers, one for each of the four subsets (I equal to 4), of 96 wells of the 384 well plates. This increases the efficiency of the chemical solution distribution system. In other embodiments, the system may be designed to process up to 864 well plates. Further, the system may also process 96 well plates while simultaneously being able to process higher density well (greater than 96 well) plates, such as 384 well plates. In such an embodiment, the table in each liquid handler is capable of aligning the pipettes with the wells of the 96 well plates and larger well (greater than 96 well) plates.

The present invention also includes a method of distributing chemical solutions, between N well plates. As above, each N well plate is considered to have I subsets of M wells where I*M equals N. One method includes aligning a subset of M wells of a first N-well plate with M pipettes of a first pipette station and aligning a subset of M wells of a second N-well plate with M pipettes of a second pipette station. The method further includes lowering the M pipettes of the first pipette station to within a desired distance of the subset of M wells of the first N-well plate and then either aspirating solution from M wells into the M pipettes or dispensing solution from the M pipettes into the M wells. The method also includes lowering the M pipettes of the second pipette station to within a desired distance of the subset of M wells of the second N-well plate and then either aspirating solution from M wells into the M pipettes or dispensing solution from the M pipettes into the M wells. The method may further include aligning a subset of M wells of a third N-well plate with M pipettes of a third pipette station and aligning a subset of M wells of a fourth N-well plate with M pipettes of a fourth pipette station. This method further includes lowering the M pipettes of the third pipette station to within a desired distance of the subset of M wells of the third N-well plate and then either aspirating solution from M wells into the M pipettes or dispensing solution from the M pipettes into the M wells. This method also includes lowering the M pipettes of the fourth pipette station to within a desired distance of the subset of M wells of the fourth N-well plate and then either aspirating solution from M wells into the M pipettes or dispensing solution from the M pipettes into the M wells.

In another method of the present invention, the above-described method may be applied to a single N-well plate. In such an embodiment, a different subset of M wells of the N-well plate may be addressed by the M pipettes of each of the first, second, third, and fourth liquid handlers. Each of these stations may aspirate or dispense solution between the subset of M wells of the single N-well plate. In the embodiment where N is equal to four times M, the four liquid handlers may be employed to sample or dispense solution between each of the N wells of the single N-well plate according to this method.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and many of the automation, computer, detection, chemistry and laboratory procedures described below are those well known and commonly employed in the art. Standard techniques are usually used for engineering, robotics, informatics, optics, molecular biology, computer software and integration. Generally, chemical reactions, cell assays and enzymatic reactions are performed according to the manufacturer's specifications where appropriate. The techniques and procedures are generally performed according to conventional methods in the art and various general references (see generally, Knuth, Donald E., *The Art of Computer Programming,* Volume 1, Fundamental Algorithms, Third Edition (Reading, Mass.: Addison-Wesley, 1997); Volume 2,

*Seminumerical Algorithms,* Second Edition (Reading, Mass.: Addison-Wesley, 1981); Volume 3, *Sorting and Searching,* (Reading, Mass.: Addison-Wesley, 1973) for computational methods. For fluorescence techniques see Lakowicz, J. R. *Principles of Fluorescence Spectroscopy,* New York: Plenum Press (1983) and Lakowicz, J. R. Emerging applications of fluorescence spectroscopy to cellular imaging: lifetime imaging, metal-ligand probes, multiphoton excitation and light quenching. Scanning Micro. Suppl Vol. 10 (1996) pages 213–24. For molecular biology and cell biology methods see Sambrook et al. *Molecular Cloning. A Laboratory Manual,* 2d ed. (1989) Cold Spring Harbor Laboratory Press, Cold Spring Harbor, N.Y. and Spector et al. *Cells a Laboratory Manual,* first ed. (1998) Cold Spring Harbor Laboratory Press, Cold Spring Harbor, N.Y. For general optical methods see *Optics Guide* 5 Melles Griot® Irvine Calif., *Optical Waveguide Theory,* Snyder & Love published by Chapman & Hall. For fiber optic theory and materials see Peter Cheo *Fiber Optics Devices and Systems,* published by Prentice-Hall, which are incorporated herein by reference which are provided throughout this document). The nomenclature used herein and the laboratory procedures in chemistry, molecular biology, automation, computer sciences, and drug discovery described below are those well known and commonly employed in the art. Standard techniques are often used for chemical syntheses, chemical analyses, drug screening, and diagnosis. As employed throughout the disclosure, the following terms, unless otherwise indicated, shall be understood to have the following meanings:

"Adaptive routing" refers to a change in the path to be followed by a work unit as a result of conditions encountered during a stage or stages of processing. Conditions could include results of previous processing steps, equipment out of order, processing priorities, or other factors. The path is the sequence of steps called for to process a work unit. For example, the path is the sequence of steps called for in the assay definition, which may be independent of specific processing equipment. System processing is typically performed at workstations, so adaptive routing allows alternative workstations to be substituted by computerized instruction.

"Operably linked" refers to a juxtaposition wherein the components so described are in a relationship permitting them to function in their intended manner. For instance, two components are mechanically linked by a conveyor means are operably linked.

"Parallel processing" refers to the routing of material flow to facilitate the simultaneous handling of multiple work units at or within multiple workstations. Parallel processing between workstations is accomplished by maintaining individual work queues within a transport system for each workstation, and allowing for many liquid handling operations to be performed simultaneously. For example, work units can be delivered in parallel to each of the workstations disposed on a transport system, while other units are queuing for subsequent operation at those workstations. Transfers from the workstations are also to be accomplished in this manner. Within workstations, many parallel instruments can perform work on a number of units simultaneously. Parallel processing of liquid samples refers to the parallel distribution or redistribution of liquid samples into a plurality of wells in at least one multiwell plate in a workstation. For instance, four parallel aspirate/dispense devices can simultaneously operate on four multiwell plates in a workstation. When the term parallel processing is used, unless explicitly stated, it does not preclude other types of processing, such as serial processing.

"Polynucleotide" refers to a polymeric form of nucleotides of at least 10 bases in length, either ribonucleotides or deoxynucleotides or a modified form of either type of nucleotide. The term includes single and double stranded forms of DNA.

"Plate" refers to a two dimensional array of addressable wells located on a substantially flat surface. Multiwell plates may comprise any number of discrete addressable wells, and comprise addressable wells of any width or depth. Common examples of multiwell plates include 96 well plates, 384 well plates and 3456 well Nanoplates™. Multiwell plates may contain either samples or chemicals such as reagents and, or, polynucleotides.

"Sample plate" refers to a plate containing a sample to be processed, such as a sample for testing or synthesis. Sample plates are usually used in a reaction module, to permit a chemical reaction, or detection of an optical property of the sample.

"Chemical plate" refers to a plate containing chemicals and, or, polynucleotides, such as a master plate with stock solutions or a daughter plate with stock solutions or dilutions thereof.

"Solid substrate" refers to a surface onto which a sample or chemical present in solution or suspension could be deposited. Substrates could include the surfaces of silicon or glass chips, or detection surfaces or sensors.

"Sample matrix" refers to a two dimensional array or pattern of sample sites, generally preset.

"Tip dispenser matrix" refers to a two dimensional array or pattern of tip dispensers generally in a preset, immobilized array, usually with at least 2 to 4 rows and 2 to 4 columns, preferably 12 rows and 8 columns for 96 well formats.

Other chemistry terms herein are used according to conventional usage in the art, as exemplified by The McGraw-Hill Dictionary of Chemical Terms (ed. Parker, S., 1985, McGraw-Hill, San Francisco, incorporated herein by reference).

Introduction

The present invention is directed towards systems and methods for the rapid distribution and redistribution of liquid samples in multiwell plates or onto substrates, typically for reformating chemical libraries. As a non-limiting introduction to the breadth of the invention, the invention includes several general and useful aspects, including:

1) a system of integrated components for the rapid aspiration and distribution of liquid samples from multiwell plates of dissimilar formats, 2) a method for reformatting the position of liquid samples present in multiwell plates.

3) a system for the rapid distribution of liquid samples to multiwell plates, and 4) a system of distributing samples, such as chemicals dissolved in a solvent, into an array or matrix on a substrate.

These aspects of the invention, as well as others described herein, can be achieved by using the devices and methods described herein. To gain a full appreciation of the scope of the invention, it will be further recognized that various aspects of the invention can be combined to make desirable embodiments of the invention. For example, the invention includes a system for the rapid redistribution of liquid samples that could be operatively linked to a storage and retrieval module or detector module. Such combinations result in particularly useful and robust embodiments of the invention.

An exemplary embodiment of chemical solution distribution system 200 according to the present invention is presented with reference to FIG. 1. The chemical solution distribution system 200 shown in FIG. 1 includes four liquid handlers 240, a programmable logic controller ("PLC") cabinet 282, solution pumps 190 and pump tubing 192, drains 242 and drain tubing 243, two plate buffers or stacker stations 260, a multiwell plate delidder/lidder station 250, bar code reader 230, operator console 280, and ingress/egress junction 270. The PLC 282 contains the logic controllers that control the operation of the each of the components of the system 200 based on operator selections entered on console 280. In the preferred embodiment of the invention, console 280 is a touch-screen console enabling an operator to view and select options for the control and processing of chemical or sample multiwell plates.

The core of an embodiment of the system 200 is described in more detail with reference to FIG. 2. The system includes a conveyor means 210 (e.g. at least one continuous conveyor belt), the conveyor means 210 moves sample plates 290 between different components of system 200 that may perform operations on the sample plate 290. In detail, delidder station 250 may remove or replace a lid (not shown) of a sample plate 290. Typically in conjunction with logic controllers, delidder station 250 tracks each lid removed with the corresponding sample plate 290. Each liquid handler is designed to either aspirate solutions from wells of sample plate 290 to pipetting heads or dispense solution from pipetting heads to wells of sample plate 290. Stacker stations 260 stack or buffer plates and can be used to increase the overall efficiency of system 200. To track sample multiwell plates, system 200 includes a bar code reader 230 as shown in FIG. 3.

Figure 3:
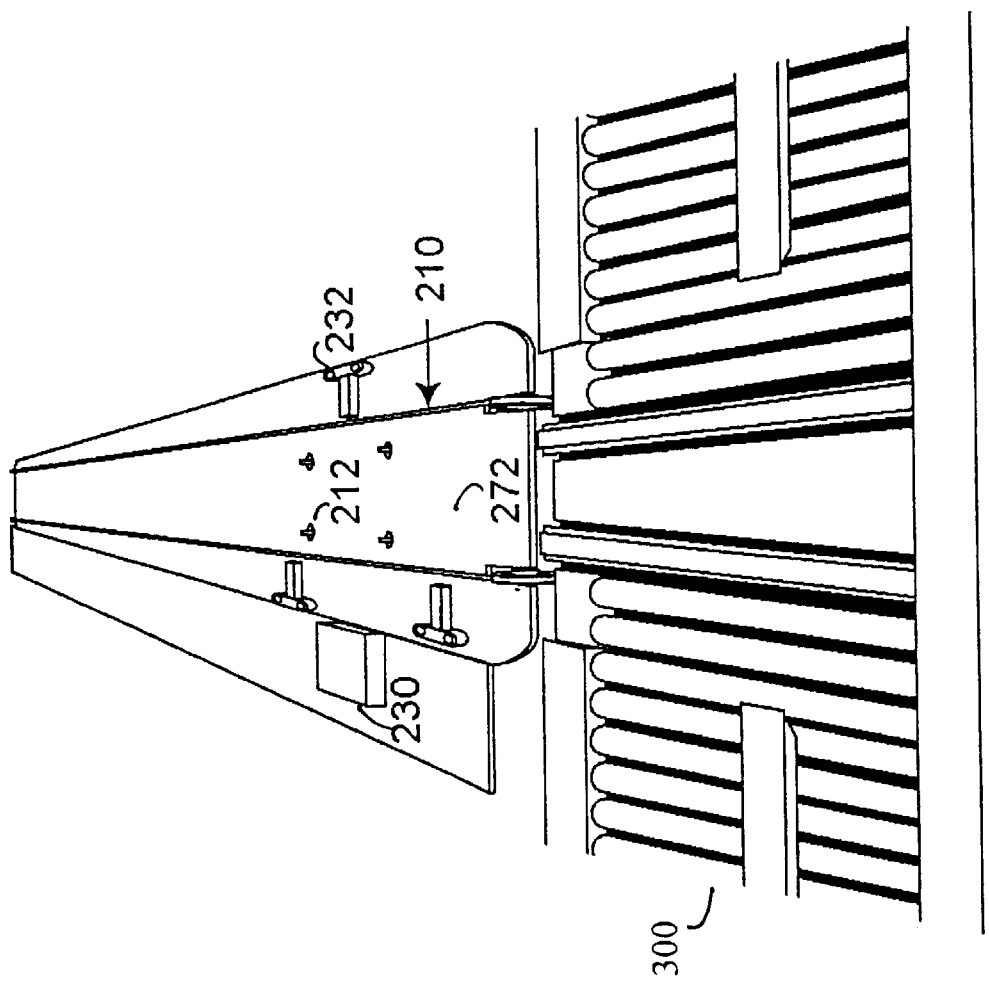
FIG. 3 is a diagram of a segment of the main section of the chemical solution distribution mechanically connected to a conveyor system to illustrate the bar code reader section.

As shown in FIG. 3, an exemplary embodiment of system 200 further includes a photosensor 232, diving board (to ensure smooth transition from the conveyer multiwell plate), 272, and stop pins 212. Photosensor 232 detects the present of sample multiwell plates on the conveyor belt 210. Upon detection of a sample plate, bar code reader 230 detects and decodes the bar code on a sample plate on conveyor 210 as is well known to one of skill in the art. The bar code information of the sample plate 290 enables system 200 to track sample plates as they are processed by the system. Upon identification of the sample plate 290, system may direct the conveyor 210 to transfer the multiwell plate to one of the processing components, i.e., delidder station 250, liquid handlers 240, and stacker station 260. The diving board 272 which is part of ingress/egress station 270 enables interconnection of system 200 as part of an automated screening system 300, such as the system described the PCT application WO 98/52047, entitled Systems and Methods for Rapidly Identifying Useful Chemicals in Liquid Samples published Nov. 16, 1998 which is hereby incorporated by reference.

As part of an automated screening system, system 200 may attach as a workstation. In a preferred embodiment of the invention, conveyor 210 includes two parallel plastic belts that travel along the length of the workstation (FIG. 2). An AC motor (not shown) turns the belts through coordination of photosensors 232, stop pins 212, and logic controller. In detail, in a preferred embodiment sixteen Keyence® Fiber Optic Sensors are used to track or check the location of sample plates in system 200. In addition, thirteen pairs of Clippard® pneumatic actuators function as stop pins 212 to position sample plates 290 at the eight different stations of system 200 (the stations includes bar code reader station 230, a delidder station 250, four liquid handlers 240, and two stacker or buffer stations 260.)

In a preferred embodiment of the invention, bar code reader 230 is a Microscan® MS710 barcode scanner. The reader 230 operates using a 5-volt power source and may communicate with a personal computer ("PC") via a RS232 cable. As noted above, delidder station 250, removes and replaces lids of sample plates 290. In detail, delidder 250 removes lids from multiwell plates 290 entering the system and replaces the lids of multiwell plates 290 when they leave system 200. In the exemplary embodiment, the delidder station 250 includes a magazine for holding up to 60 lids, a lifting device (not shown), and retaining pads (not shown). In operation, the lifting device, located directly below the conveyor 210 employs a bi-directional motor that lowers and raises four pins. Lids are captured and replaced by delidder 250 by raising and lowering the height of the four pins. Usually, two optical sensors are positioned below the retaining pads to coordinate the employment of the retaining pads during the movement of a lid. As noted above, system 200 also includes two stacker or buffer stations 260 that are used to store multiwell plates. Storing multiwell plates 290 enables system 200 to perform complex operations on multiwell plates. In an exemplary embodiment, each stacker may store fifty standard depth multiwell plates or seventeen deep well multiwell plates. Similar to delidder 250, each stacker or buffer 260 also employs four pins and retaining pads to capture and transport multiwell plates 290 (instead of lids). In the preferred embodiment, the lifting devices of the stackers include two Bimba Flat-1 FS 040.5 XH pneumatic actuators. Of the components that process sample multiwell plates 290, liquid handlers 240 perform the primary function of system 200, i.e., distribution of chemicals or samples between sample plates 290.

Figure 4:
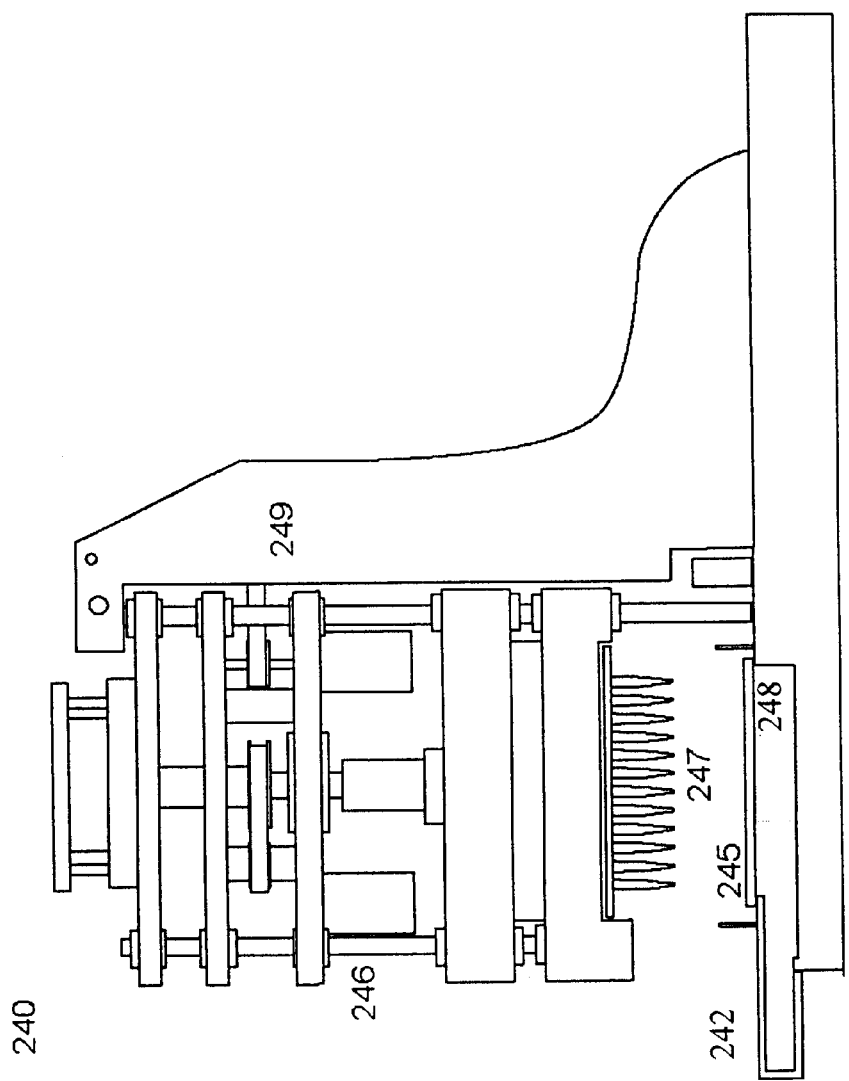
FIG. 4 is a diagram of an exemplary liquid handler or liquid handling according to the present invention and shown in FIG. 1 and FIG. 2.

An exemplary liquid handler 240 is presented with reference to FIG. 4. The exemplary pipette station 240 includes a drain 242, wash station 245, Z-axis motor 246, pipettes on a head 247, movable table or platen 248, and D-axis motor 249. In this embodiment, Z-axis motor 246 controls the height of the pipettes 247 relative to the wash station 245 and multiwell plate 290 when a plate 290 is positioned in a liquid handler 240. Alternatively, though not preferred the table can include a Z-axis motor to vary the height. The height of the pipettes relative to the multiwell plate 290 may vary for differently sized multiwell plates with particular well densities. In an exemplary embodiment, the Z-motor axis is a 1.7 volt 4.7 Amp bi-directional servomotor. The D-axis motor 249 is used to control the amount of solution aspirated into or dispensed from pipettes 247. The D-axis motor 249 is also a 1.7 volt 4.7 Amp bi-directional servomotor. In detail, the motor is coupled to pistons that produce air displacement in pipettes 247 to control aspiration or dispensation of solution. It is noted that the present invention can support different pipette types. In this embodiment, each station 260 has 96 pipettes in an eight by twelve rectangular configuration. Pipettes 247 are positive displacement fixed probes having 200, 50 or 20 microliter capacities. As noted above, each station also has a wash station 245 and drain 242. The wash station includes 96 chimneys that well up and spill over when a pump 190 is operating. The overflow spills into the drain 242 and then drain tubing 243. In the preferred embodiment, each liquid handler 240 has a different pump 192 enabling a different buffer or dimethylsulfoxide ("DMSO") to be provided by each wash station 245. This increases the ability of system 200 to perform more complex operations efficiently. Each liquid handler also has an independently movable platen or table 248. Alternatively, though not preferred, the liquid handling can move in the X or Y direction, as set forth herein.

The table engages a multiwell plate 290 when it enters a station 240. As described with reference to FIG. 5A and FIG.

5B, table 248 enables each liquid handler 240 to process multiwell plates 290 having a number of wells equal to a multiple of the number of pipettes heads. For example, if a multiwell plate having N wells is to be processed by a station having M pipettes where M is an integer multiple, I of N, then table 248 would need to align or address the pipettes with I different subsets of M wells that comprise the N wells of the multiwell plate to be processed. As noted above, exemplary liquid handlers 240 have 96 (M=96) pipettes. Depending on the addressable positions of table 248, each station 240 may process sample multiwell plates having a number of wells equal to an integer multiple of 96. In the preferred embodiment, each station 240 may process multiwell plates having 96 or 384 (4*96) wells 291.

Figure 5A:
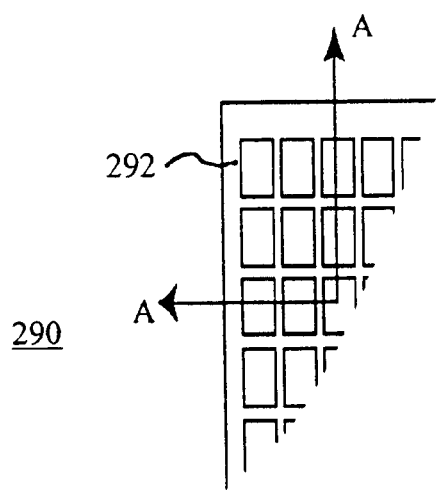
FIG. 5A is a partial diagram of an exemplary 384-well sample or chemical plate.
Figure 5B:
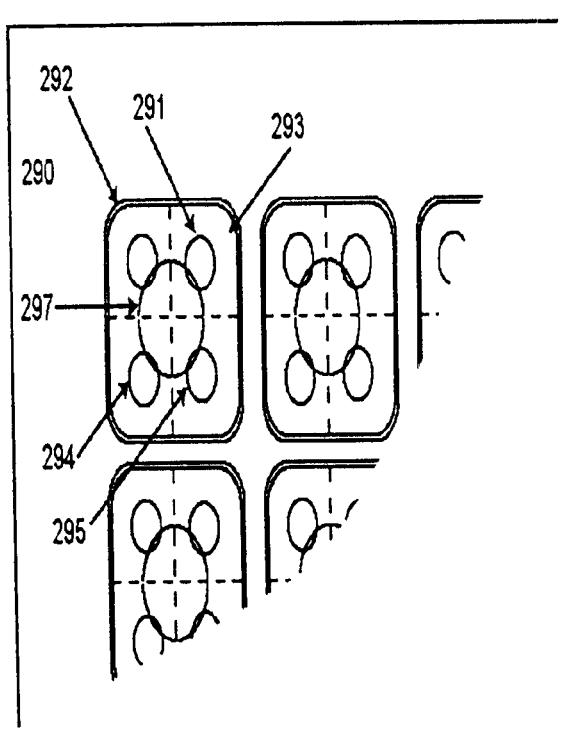
FIG. 5B is a section A—A of the exemplary 384-well chemical plate shown in FIG. 5A.

A partial diagram of an exemplary 384-well sample multiwell plate 290 is shown in FIG. 5A. The multiwell plate is rectangular having a 16 by 24 configuration. A standard 96-well plate (not shown) has an 8 by 12 configuration. In order to address the 384 wells of a 384-well plate, the plate is subdivided into four (I=4) subsets of 96 wells as shown in FIG. 5B. Table 248 can be positioned to align any subset of 96 wells with the 96 pipettes. Thus, table 248 may address any of the four subsets of wells shown as quadrants 292, 293, 294, and 295 in FIG. 5B. FIG. 5B also shows the position 297 of a well of a corresponding standard 96-well plate is centered relative to the four subsets of 96 wells of a 384 well plate. Thus, to address both a standard 96-well plate and 384-well plates, tables 248 each address five different positions: center, upper left quadrant, upper right quadrant, lower left quadrant, and lower right quadrant. The combination of the movable tables 248 and separate pumps 192 for wash stations 245 of each liquid handler 240 and conveyor 210 enables system 200 to efficiently handle complex operations involving groups of 384-well plates and 96-well plates simultaneously. For example, four different 384-well plates may be simultaneously processed by each liquid handler 240. Each station may align the 96 pipettes 247 with any of the four subsets of 96 wells of the 384 well plates by moving the multiwell plate via table 248. Then, solution may be aspirated from or dispensed to the four, different 384-well plates. In another example, four 96-well master plates may be simultaneously processed by the four liquid handlers 240 to aspirate or dispense solution. Also, a single 384-well plate may be processed by all four liquid handlers 240 in sequential or serial order where each station 240 processes a different one of the four subsets of 96-wells by aspirating or dispensing solution in each subset.

Figure 6A:
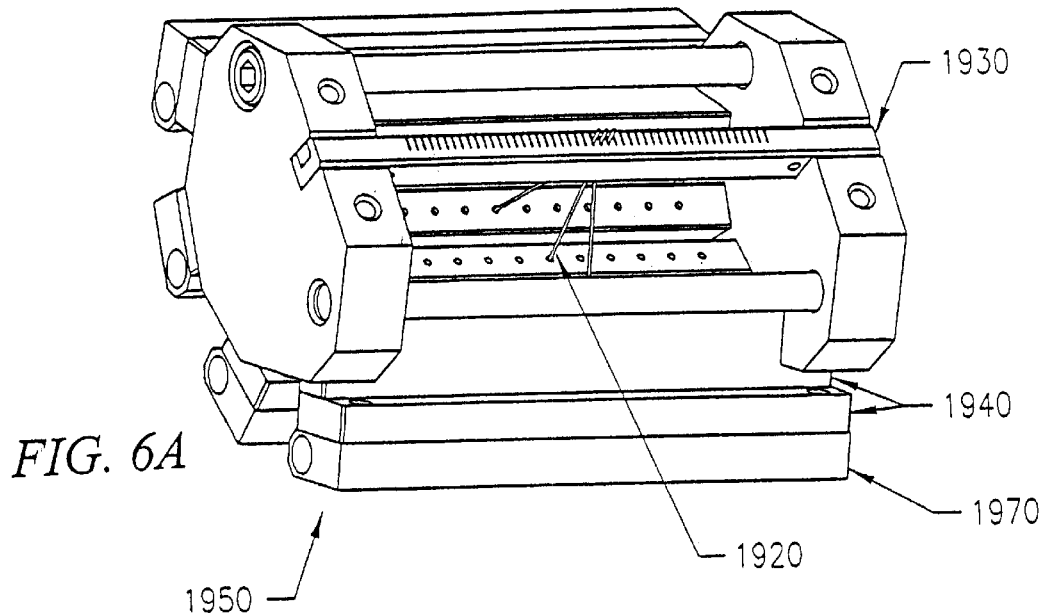
FIG. 6A (perspective view of assembled unit) and B (exposed view of one bank) shows components of another embodiment of a chemical solution distribution apparatus.
Figure 6B:
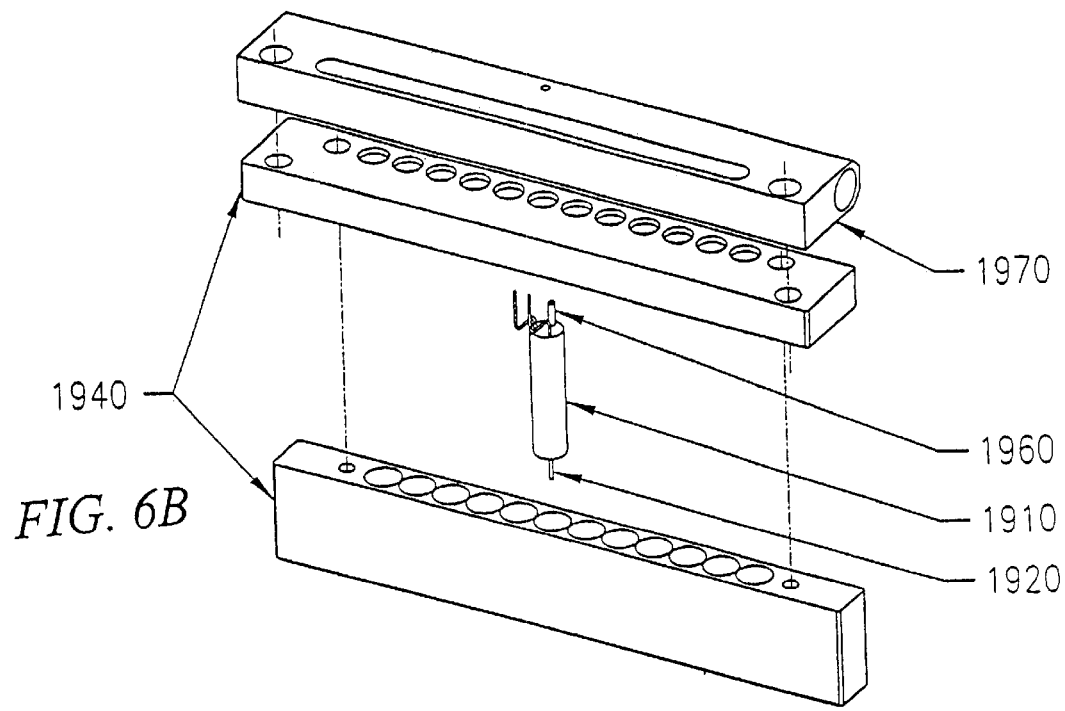

FIG. 6A (perspective view of assembled unit) and B (exposed view of one bank) shows components of another embodiment of a sample distribution apparatus that includes valves 1910, valve tips 1920 (straight tip in FIG. 6B, bent tip in FIG. 6A), tip block 1930, valve block 1940, valve block assembly 1950, fluid lines 1960, and fluid manifold 1970, fluid reservoir 1980, and pressure system are not shown. In a preferred embodiment (48 valve linear array), four linear arrays of 12 valve (banks) each are placed side by side. The valves and pipette tips in each of these arrays are spaced 6 mm apart and each array is staggered 1.5 mm in relation to each other. The tips of the valves are configured to share the same fluid path configuration and align together into a linear array of 48 tips spaced 1.5 mm apart. The tips from a single bank of valves are spaced 6 mm apart and are arranged as every fourth tip in the 48-tip array.

Another embodiment uses larger valves that would require larger spacing between each valve. The tips in this embodiment would use flexible tubing to connect the valve and tips. Each valve can be individually controlled to allow different patterns of dispensing. Though designed to dispense into a 48 well per column plate, this array could also dispense into other multiwell plate configurations. For example, 864-well plates (24 by 36 wells), 384-well plates (16 by 24 wells) or 96-well plates (8 by 12 wells) are compatible by using every second, third or sixth valve, respectively. If the multiwell plate can be moved in the Y as well as the X direction, then each 48 valve linear array can dispense up to four different reagents by plumbing a different reagent into each of the four banks of 12 valves. Moving the multiwell plate in both the X and Y directions allows each well to align with a pipette tip from each bank. If the plate can only be moved in the X direction, then the following dispensing arrangements are possible with a 48-pipette array (see FIG. 7).

96-Well Plate (6.5 mm Diameter Wells) Multiple Reagent Mode

A single 48 valve linear array can deliver up to four different reagents into a 96-well plate since a single bank can deliver into each well. Each bank is plumbed to receive a different reagent. Plate can be secured properly in the Y direction for each reagent and the multiwell plate does not need to move in the Y direction during the dispensing of that one reagent.

384-Well Plate (3.4 mm Diameter Wells) Single Reagent Mode

Valves from each bank must be used in order to dispense into each well of a 384-well plate; therefore only one reagent can be dispensed from the 48-pipette array.

864-Well Plate (Approximately 2.0 mm Diameter Wells)

Each well can be accessed by using either banks 1 and 3 or banks 2 and 4. This allows two different reagents to be delivered if the multiwell plate is aligned properly in the Y direction for each reagent. In operation, the linear array of pipettes can be positioned over a high-density plate, e.g., 48 by 72-well plate. The wells in this multiwell plate are spaced identically to the pipettes (1.5 mm apart). The pipettes are activated and a reagent is dispensed simultaneously into each well in one column. The multiwell plate is then moved over one column and the pipettes are again activated. This is repeated over the entire multiwell plate. The amount dispensed is controlled by the valve opening time and the pressure feeding the reagent to the valves (other factors also control dispensed volumes, particularly restrictions to flow). Variable amounts can be dispensed into each well by controlling the timing of valve opening and the dispensation pattern across the linear array of valves. Each pipette of the linear array can be individually controlled via software. The entire fluid path can be flushed clean by first purging the four fluid manifolds, followed by each of the 48 valves. Three 3-way valves (two on the input side and one on the output side of the fluid manifolds) will allow flushing with a wash liquid and with air. The device can be cleaned between reagent changes and for long-term inactive periods. The valve assembly can be designed in a modular form in order to facilitate replacement and repair of single valve/tip components and/or whole banks of valves. The fluid path dead space is preferably designed to minimize flush out volumes.

In another embodiment, the pipette tip pitch can be modulated via a cam shaft mechanism which enables on-the-fly control of pipette tip spacing.

In another embodiment, each valve array can contain a different reagent and address the dispensation requirements of the assay by additional positioning movements under the linear array pipette.

In one additional embodiment, the sample distribution apparatus can rapidly dispense or aspirate large numbers of small volume samples, around 10 to 50 nanoliters to, and from, multiwell plates of different well densities to enable efficient distribution of chemical samples.

Component Functions

Aspiration or dispensation into multiwell plates of different densities is accomplished by automated orthogonal positioning of a multiwell plate such as shown in FIG. 5A and FIG. 5B. Typically, the multiwell plates are securely disposed on an orthogonal positioner or table 248 that moves the wells of a multiwell plate with a first density in an X, Y position with respect to the X, Y position of the liquid handler. Usually, the liquid handler will have an array of aspiration and/or dispensation pipettes 240.

Many aspiration/dispensation pipettes can operate simultaneously in parallel. The orthogonal positioner will align each well with the appropriate pipetting head. Preferably, a predetermined location (e.g., center) of a pre-selected addressable well will be aligned with the center of pipetting head's fluid trajectory. Other alignments can be used, such as those described in the following examples. With a pipetting head substantially smaller than a well diameter, orthogonal positioning permits aspiration or dispensation into multiwell plates of different densities and well diameters.

An orthogonal positioner or table can typically match an array of pipettes with an array of wells in X, Y using a mechanical means to move the wells into position or the liquid handler (e.g., dispensing heads) into position. Preferably, arrays of wells on a multiwell plate are moved rather than the liquid handler. This design often improves reliability, since multiwell plates are usually not as heavy or cumbersome as liquid handlers, which results in less mechanical stress on the orthogonal positioner and greater movement precision. It also promotes faster liquid processing times because the relatively lighter and smaller multiwell plates can be moved more quickly and precisely than a large component. The mechanical means can be a first computer-controlled servo-motor that drives a base disposed on an X track and a second computer-controlled servo motor that drives an Y track disposed on the X track. The base can securely dispose a multiwell plate and either a feedback mechanism or an accurate Cartesian mapping system, or both that can be used to properly align wells with pipettes. Other such devices, as described herein, known in the art or developed in the future to accomplish such tasks can be used. Usually, such devices will have an X, Y location accuracy and precision of at least 0.1 mm in X and 0. 1 mm in Y, preferably of at least 0.03 mm in X and 0.03 mm in Y, and more preferably of at least 0.01 mm in X and 0.01 mm in Y. It is desirable that such devices comprise detectors to identify the wells or multiwell plates being orthogonally positioned. Such, positioners for predetermined X, Y coordinates, can be made using lead screws having an accurate and fine pitch with stepper motors (e.g., Compumotor Stages from Parker, Rohnert Park, Calif., USA). Such motors can be computer-controlled with the appropriate electrical inputs to the stepper motor. Orthogonal positioners can be used with other components of the invention, such as the reagent pipette or detector to position sample multiwell plates.

Alternatively, a liquid handler can be disposed on a Z-positioner, having an X, Y positioner for the liquid handler in order to enable precise X, Y and Z positioning of the liquid handler (e.g., Linear Drives of United Kingdom). A reference point or points (e.g., fiducials) can be included in the set up to ensure that a desired addressable well is properly matched with a desired addressable head. For instance, the multiwell plate, the orthogonal positioner or the liquid handler can include a reference point(s) to guide the X, Y alignment of a multiwell plate, and its addressable wells, with respect to the liquid handler. For example, the liquid handler may have a detector such as a camera (not shown) that corresponds in X, Y to each corner of a multiwell plate. The multiwell plate may have orifices (or marks) that correspond in X, Y to the liquid handler's position detectors. The multiwell plate's orifices allow light to pass or reflect from a computer-controlled identification light source located on the orthogonal positioner in the corresponding X, Y position. Optical locators known in the art can also be used in some embodiments, such as described in PCT patent application WO91/17445 (Kureshy), which is hereby incorporated by reference. Detection of light by the liquid handler emitted by the orthogonal positioner verifies the alignment of the multiwell plates. Once multiwell plate alignment is verified, aspiration or dispensation can be triggered to begin. Stepper motors can be controlled for some applications as described in U.S. Pat. No. 5,206,568 (Bjornson), which is hereby incorporated by reference.

When handling multiwell plates of different densities, it is desirable to track the multiwell plate density with a database linked to a plate bar code (or some other plate identification system, e.g., radio frequency) and to provide a sample distribution apparatus that can register the bar code. Bar code labels are typically positioned on the narrow end of the multiwell plates, column 12 side, and in a 3 to 1 ratio, 0.25"×1.0", 10 mil bar code 128, such as those from Intermec, Everett, Wash. When used with a data processing and integration module controller, the bar code can easily reference a plurality of multiwell plate and well information from the data store, such that no encoded data is necessary on the bar code itself. Misread or unreadable labels produce an error code available to the supervisory control system. The sample distribution apparatus can then be properly instructed to aspirate or dispense in a manner that corresponds to the well density of the multiwell plate. This permits aspiration at one well density and dispensation at a second well density. Thus, compression of low density multiwell plates can occur by the transfer of liquids to a higher density multiwell plate and expansion of high density multiwell plates can occur by transfer of liquids to a lower density multiwell plate. This feature advantageously allows a sample distribution apparatus to functionally interface with other workstations that may individually utilize multiwell plates of different well density. For example, traditional 96-well plates can be used to store chemical solutions in master plates in a storage and retrieval module. The sample distribution apparatus may aspirate a predetermined volume of chemical solution from all the addressable chemical wells of a master plate. The sample distribution apparatus may then dispense a predetermined volume of chemical solution into a pre-selected portion of the addressable wells of a 384 daughter plate (i.e. compression). This process can be repeated to construct replicate arrays on the same or different daughter plate.

In one embodiment, the liquid handler may comprise a plurality of nanoliter pipettes that can individually dispense a predetermined volume. Typically, pipettes are arranged in two-dimension array to handle multiwell plates of different well densities (e.g., 96, 384, 864 and 3,456). Usually, the dispensed volume will be less than approximately 2,000 nanoliters of liquid that has been aspirated from a predetermined selection of addressable chemical wells and dispensed into a predetermined selection of addressable sample wells. Preferably, nanoliter pipettes can dispense less than approximately 500 nanoliters, more preferably less than approximately 100 nanoliters, and most preferably less than approximately 25 nanoliters. Dispensing below 25 nanoliters can be accomplished by pipettes described herein. Preferably, minimal volumes dispensed are 5 nanoliters, 500 picoliters, 100 picoliters, or 10 picoliters. It is understood that pipettes capable of dispensing such minimal volumes are also capable of dispensing greater volumes. The maximal volume dispensed may be largely dependent on the dispense time, reservoir size, tip diameter and pipette type. Maximum volumes dispensed are about 10.0 microliters, 1.0 microliters, and 200 nanoliters. Preferably, such liquid handlers may be capable of both dispensing and aspirating. Usually, a nanoliter pipette (or smaller volume pipette) comprises a fluid channel to aspirate liquid from a predetermined selection of addressable wells (e.g., chemical wells). Liquid handlers are further described herein, and for some volumes, typically in the microliter range, suitable liquid pipettes known in the art or developed in the future can be used. It may be particularly useful to use liquid handlers capable of handling about 1 to 20 microliter volumes when it is desired to make daughter plates from master plates. Preferably, in such instances a liquid handler has a dispensing nozzle that is adapted for dispensing small volumes and can secure a tip having a fluid reservoir.

In one embodiment, nanoliter pipettes comprise solenoid valves fluidly connected to a reservoir for liquid from an addressable chemical well. The fluid reservoir can be a region of a pipette tip that can hold fluid aspirated by the nanoliter pipette. Usually, a tip reservoir may hold at least about 100 times the minimal dispensation volume to about 10,000 times the dispensation volume and more preferably about 250,000 times the dispensation volume. The solenoid valves control a positive hydraulic pressure in the reservoir and allow the release of liquid when actuated. A positive pressure for dispensation can be generated by a hydraulic or pneumatic means, e.g., a piston driven by a motor or gas bottle. A negative pressure for aspiration can be created by a vacuum means (e.g., withdrawal of a piston by a motor). For greater dispensing control, two solenoid valves or more can be used where the valves are in series and fluid communication.

In another embodiment, nanoliter pipettes comprise an electrically sensitive volume displacement unit in fluid communication to a fluid reservoir. Typically, the fluid reservoir holds liquid aspirated from an addressable chemical well. Electrically sensitive volume displacement units are comprised of materials that respond to an electrical current by changing volume. Typically, such materials can be piezo materials suitably configured to respond to an electric current. The electrically sensitive volume displacement unit is in vibrational communication with a dispensing nozzle so that vibration ejects a predetermined volume from the nozzle. Preferably, piezo materials are used in pipettes for volumes less than about 10 to 1 nanoliter, and are capable of dispensing minimal volumes of 500 to 1 picoliter. Piezo pipettes can be obtained from Packard Instrument Company, Connecticut, USA (e.g., an accessory or the MultiProbe 104). Such devices can also be used in other liquid handling components described herein depending on the application. Such small dispensation volumes permit greater dilution and conserve and reduce liquid handling times. In some embodiments, the liquid handler can accommodate bulk dispensation (e.g., for washing). By connecting a bulk dispensation means to the liquid handler, a large volume of a particular solution may be dispensed many times. Such bulk dispensation means are known in the art and can be developed in the future.

The liquid handler may be disposed on a Z-dimensional positioner to permit adjustments in liquid transfer height. This feature allows for a large range of multiwell plate heights and aspirate and dispense tips, if desired, to be used in the sample distribution apparatus. It also permits the dispense distance between a well surface, or liquid surface in a well, and a liquid handler to be adjusted to minimize the affects of static electricity, gravity, air currents and to improve the X, Y precision of dispensation in applications where dispensation of a liquid to a particular location in a well is desired.

Alternatively, multiwell plates can be positioned on a Z-dimensional positioner to permit adjustments in liquid transfer height. Static neutralizing devices can also be used to minimize static electricity. Generally, the liquid transfer height will be less than about 2 cm. Preferably, small volumes will be dispensed at a liquid transfer height of less than about 10 mm, and more preferably less than about 2 mm. Occasionally, it may be desirable to contact the tips with a solution in a controllable fashion, as described herein or known in the art.

The sample distribution apparatus may also be structured to minimize contamination. The liquid handler can be constructed to offer minimum tip exposure to liquids using a sensor (e.g., acoustic, and refractive index). For instance, probe contact with a liquid surface can be reduced by providing a liquid sensor on the pipetting tip, such as a conductivity or capacitance sensor, that forms a feedback system to control the entrance of a tip into a liquid. Carry-over from one multiwell plate to another multiwell plate can be kept to acceptable level with a blow-out of the tip and minimizing tip penetration into a liquid with a sensor. Preferably, a sample distribution apparatus will include a means for volume control, and washing the liquid handler. Alternatively, the data processing and integration module can calculate the remaining levels in the wells based on usage and predicted evaporation, in order to deploy the tips to suitable measured distance and can be adjusted for multiwell plates of different heights.

In most embodiments, it will be advantageous to integrate and operably link the sample distribution apparatus with at least one other workstation. The integration can be accomplished with a computer and associated control programs to instruct and coordinate the functions of the liquid handler. For implementation with a liquid processing system, a data processing and integration module type device may be used as described herein, as well as other computing devices capable of integrating instrumentation as known in the art or developed in the future.

Alternatively, a reaction module may be used without directly integrating to another workstation by tracking addressable wells in groups and either mechanically or manually transporting addressable wells to another workstation where the addressable wells are identified. For instance, the reaction module may be directly integrated and operably linked to a storage and retrieval module and sample transporter, and indirectly linked to a separate detector through manual operations. While this approach is feasible, especially for lower throughputs, it is not desirable for higher throughputs as it lacks direct integration that can lead to faster throughput times. Manual operations also are more frequently subject to error especially when processing large numbers of samples. Preferably, the reaction module can be integrated with other workstations and operate in a mode with minimal or substantially no manual intervention related to transferring addressable wells to other workstations.

As noted above, FIG. 1 and FIG. 2 show one embodiment of a sample distribution apparatus 200 with a conveyor means 210 comprising a rotating band that runs the length of the sample distribution apparatus platform 220 and can transport multiwell plates. A bar code reader 230 registers multiwell plates on the conveyor means. A series of liquid handlers 240 are disposed along the conveyor means. Addressable wells in four chemical multiwell plates can be simultaneously aspirated from the liquid held in the liquid handlers, and then dispensed in additional plates. Lids can be removed or replaced by the delidder/lidder 250. Proximal multiwell plate stacker 260 and distal multiwell plate stackers 260 can be used temporarily to store multiwell plates, such as chemical and sample plates, which can facilitate multiwell plate selection. The sample distribution apparatus can be operably linked to a sample transporter at an ingress/egress junction 270.

Plate Buffers

Figure 2:
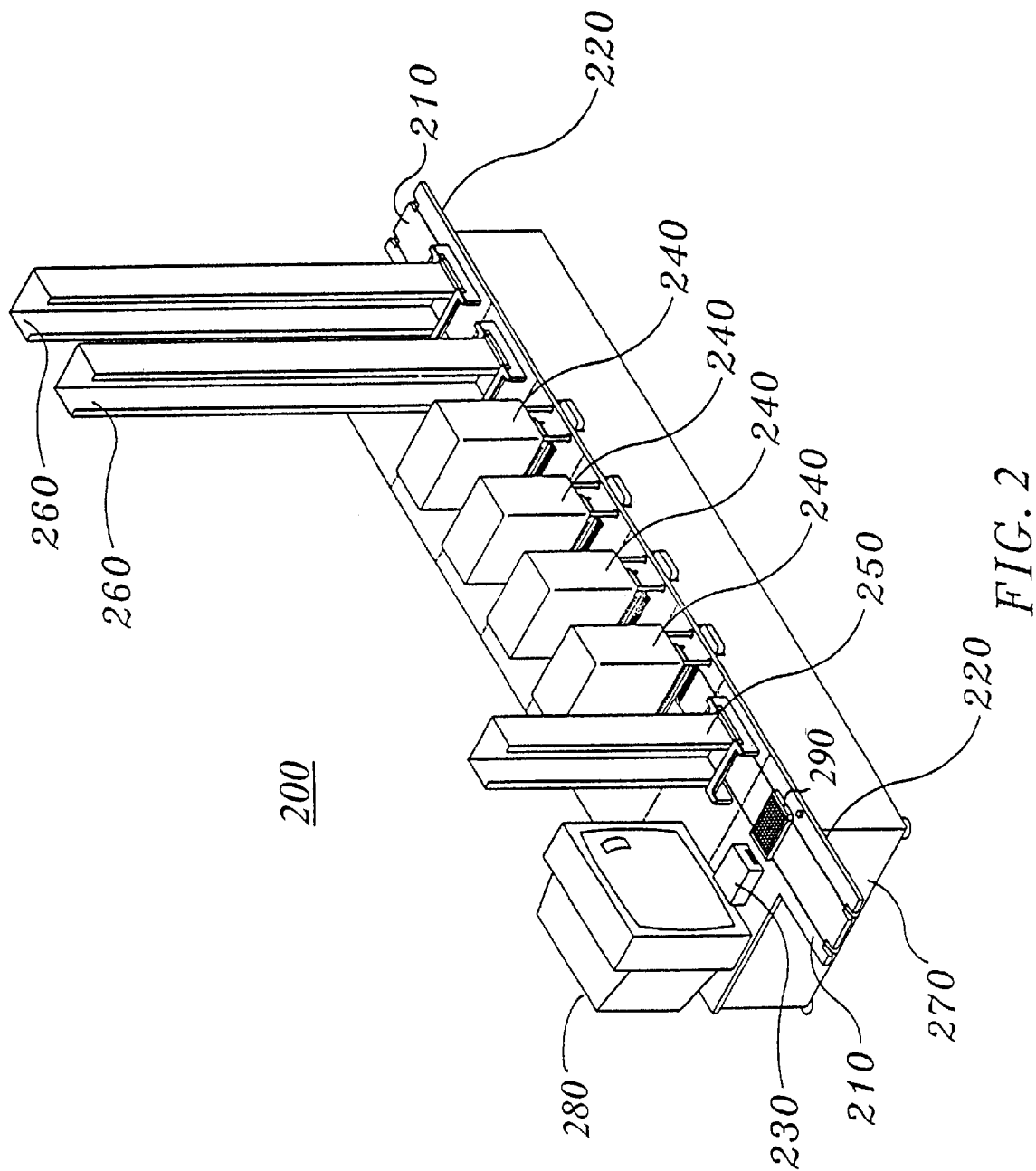
FIG. 2 is a diagram of the main section of the chemical solution distribution system shown in FIG. 1.

As noted and shown in FIG. 1 and FIG. 2, the sample distribution apparatus 200 may also include one or more multiwell plate buffers 260 (e.g., stackers). The buffer 260 acts as a temporary storage depot for addressable wells or multiwell plates. Preferably, plate retrieval from a plate buffer will be predetermined. Multiwell plate retrieval can be either dependent or independent of the order of selection and can be computer-controlled. Preferably, the data processing and integration module may include an adaptive processing and or parallel processing routine to reduce storage and retrieval time, as described herein. It is also desirable to provide for a routine to reduce transport time of any well retriever used in a storage and retrieval module. By allowing a multiwell plate buffer to acquire addressable wells as they are retrieved by a storage and retrieval module, the transport routine of the storage and retrieval module can be designed to minimize retrieval time rather than to retrieve addressable wells in a sequential order. Also, a stacker may also be used as a multiwell plate buffer. Typically, a plate stacker will up/down stack multiwell plates of a standard footprint and with different densities (e.g., deep well (e.g., 5 cm) or shallow well multiwell plates of 96 (e.g., 1 cm), 384, 864, 1536, and 3,456 (e.g., 1 to 3 mm) well format or greater (e.g., 9,600). A computer control system will track stacker contents. The apparatus 200 may also include a delidder 250 to remove lids on lidded plates.

Conveying Surface

In one embodiment the invention can be used with a conveying surface that can transport addressable wells on multiwell plates, between the invention and other workstations. Typically, the conveying surface will comprise at least two parallel sample transporter lanes, and preferably at least four parallel lanes. Typically, a sample transporter lane can transport plates in both directions (e.g., north and south movement in the same lane but at different times) by changing the transport direction. It will, however, be desirable in some instances to dedicate one or more lanes, to unidirectional transport to reduce transition times associated with changing transport direction. Each lane can be disposed, with one or more intersections that permits transport of multiwell plates in and out of each lane. Such intersection can be used to route multiwell plates to workstations. Typically, at least one or two workstations will be operably linked to the sample transporter, however, more workstations (e.g., 3 to 6 or more) can be operably linked to obtain maximum benefit from flexible routing with intersections and parallel processing of complex processes.

In one embodiment, the conveying surface is a reduced friction, ortho-multilane conduit. In this embodiment, the conveying surface uses multiple lanes to transport multiwell plates straight to a destination point, preferably not in a rotary fashion. Such lanes can be used to create processing grids comprised of intersections and highways to direct the trafficking of multiwell plates. Preferably, such grids are located in the same plane but multi-plane grids can be used. Although transport in each lane can be stopped to permit passage of a multiwell plate through an intersection, each lane is a continuous conduit that allows multiwell plates to flow. The multiwell plates can rest on a moving surface of the conduit or can be secured either on the conduit's surface or side, so long as the conduit's surface allows for transport. For ease of overall operation, the flow of the multiwell plates can be computer-controlled. In some limited, simple applications a lane may be simply activated or deactivated by the presence of an object as a multiwell plate without utilizing a computer.

Preferably, the conduit uses a surface material to reduce friction to minimize the force required for movement and to increase the smoothness of transport to reduce spills, contamination, and to allow for settling of well contents if so desired. Such materials include Teflon and Delrin. The materials can be used as rollers or moveable bases connected to a track that forms a lane. The transport capacity of the conveying surface should be commensurate with the intended throughput of the system to which it is operably linked. For instance, the rate of multiwell plate transport for standard multiwell plates is typically at least about 6 meters per minute, and preferably at least about 15 meters per minute. Lanes are typically about 15 to 25 cm in width and preferably about 1 to 5 meters based in length that may be based on queuing requirements.

Computer Control

In one embodiment, the screening sample distribution apparatus further includes a programmable logic controller, 282 with ladder logic having a minimum of two RS-232 ports open for external communication and programming (or GPIB interfaces). The programmable logic controller with ladder logic may also have an Ethernet communication card enabling the programmable logic controller to communicate with another computer via transmission control protocol/internet protocol. The programmable logic controller may have four discrete inputs and three discrete outputs open for handshaking to a conveyor system.

Failure of the sample distribution apparatus to perform any programmed function within an allotted time may constitute an error. Performance of a function outside of measurable parameters may also constitute an error. Errors may be corrected automatically when within the ability of the instrument to do so. The user may be notified of unrecoverable errors via both the touch screen and the external link. In addition, the apparatus may set the handshaking logic to refuse further multiwell plate input until the error is corrected. For given families of error conditions, a response may be specified, e.g., for recoverable errors, such as bar code errors. For errors that are automatically recoverable, response parameters may exist to either pause the instrument and report the error, to automatically recover from the error, or report/log the error and resume operation. Recoverable errors will have a time-out function to halt recovery, if time exceeds a configurable value. The control software can control the parameters as specified in Table 1, via an interface. Level two will facilitate the same function via an external computer.

TABLE 1

| Bar Code | Conveyor | Delidder | Aspirate | Aspirate Range | Dispense | Dispense Range | Stacker |
|---|---|---|---|---|---|---|---|
| Read | ON/OFF | Up/Down | Z Height (mm) | −30 to 60 | Z Height (mm) | −30 to 60 | Up/Down |
| Compare | Forward/Reverse | | Volume ($\mu$L) | 0 to 200 | Volume ($\mu$L) | 0 to 200 | |
| Exception | | | Speed (%) | 0 to 100 | Speed (%) | 0 to 100 | |
| | | | Overfill ($\mu$L) | 0 to 200 | | | |
| | | | Air Gap ($\mu$L) | 0 to 200 | | | |
| | | | Pre-Dispense ($\mu$L) | 0 to 200 | | | |
| | | | Plate/Bath | 0 or >0 | | | |

A sample distribution apparatus can include integrated computer control for managing and directing the entire dispense operation. The linear array pipette and its integrated positioning requirements can use sophisticated computer control for effective operation. The computer not only monitors the status of key sensors (e.g., reagent bottle pressure, liquid level, multiwell plate position, and positioning limit switches) but also provides the interface for generating specific liquid dispensation patterns and volumes to the high density multiwell plate. Timing of dispensation can be accomplished by a variety of means known in the art and developed in the future, so long as such timing means are suitable for the time frame and control desired. For example, the National Instruments AT-MIO-16XE-50 board can be used as timing means to send timing signals to two of their AT-DIO-32F boards. The 64 ports on these 32F boards are kept normally high and send out timed low signals. An inverter board is used to make the timed portion high and these high signals are used to close high voltage relays (Opto ODC5A) which run the valves. An OV'R driver (Lee Company cat #DRVA0000010A) is used to protect the valves from overheating during prolonged open periods.

The software controlling the valves (or pipettes) can be written to integrate into a screening system or for a standalone use. Software for laboratory instrumentation is known in the art and can be used. For example, software can be written in LabVIEW (National Instruments, TX, USA). The user selects a valve opening time and the valves to be opened. This program can be embedded within a larger program that controls other features (such as the X, Y positioner) to obtain an automatic pipette.

System Operations

The sample distribution apparatus 200 may be used to perform any different operations. For example, the apparatus may be used as a screening sample distribution apparatus. A screening sample distribution apparatus permits the preparation of multiwell plates or substrates with samples including chemicals, such as test chemicals from addressable chemical wells and biological reagents (e.g., cells or isolated molecular targets) or polynucleotides. The primary function of the screening sample distribution apparatus is to rapidly aspirate solutions from one multiwell plate and transfer them into another multiwell plate or substrate. This is usually accomplished with an array of 96 pipettors arranged in a liquid handling head. Typically the pipettors are designed to be substantially smaller in diameter than that of a 96 well diameter to enable maximum positional flexibility when formating from well size and density to a second well density and size. In one embodiment, the array of pipette heads 247 is most preferably M liquid handlers by N liquid handlers, wherein M is the number of addressable wells in a column on a multiwell plate or an integer multiple thereof and N is the number of addressable wells in a row on such multiwell plate or an integer multiple thereof (wherein M and N preferably have the same integer multiple), as described herein. The screening sample distribution apparatus can be operably linked to other workstations with a sample transporter 300, which is also shown in FIG. 3.

The sample distribution apparatus for both aspiration and dispensing in one embodiment comprises pipettes, stackers, a liquid handler, a reader and a conveyor. In one embodiment, the screening sample distribution apparatus is designed with a liquid handler, having 96-pipettes (pipette heads) that may use positive displacement disposable tips in 200 $\mu$L, 50 $\mu$L and 20 $\mu$L volumes. Presently, a disposable 200 $\mu$L tip head can deliver a range of volumes of 1 $\mu$L to 200 $\mu$L, with precision and accuracy of 10% at 1 $\mu$L to 3% at 200 $\mu$L. An optional disposable 20 $\mu$L tip can deliver a range of volumes of 0.1 $\mu$L to 20 $\mu$L, with precision and accuracy of 10% at 0.1 $\mu$L to 3% at 20 $\mu$L. The pipette can move in Z-axis (vertical axis, i.e. perpendicular to plane of a floor), which is controlled with a Z-positioner and has a travel distance from below a conveyor, to access a wash station or reagent trough, to above the conveyor. Preferably, a lidded deep well multiwell plate can pass underneath (about 3 to 5.5 cm in distance). The dispense axis (the axis with respect to volume displacement) will be at least 10,000 steps (servo-motor) to displace the full pipetting volume. Dispensing speeds are controlled by positive movement of a shaft and are controllable from 1 mm/second to 50 mm/second. The resolution of the z-axis will be at least 25,000 steps over a 75 mm travel from below the conveyor to a fully retracted position.

Positional feedback may be required for both Z and D-axis (dispense axis), such as encoders, liquid level and limit switches. Both axes may be capable of simultaneous and concurrent operation independent of each other. The pipette assembly must be continuously adjustable (no detentes or stops) in "X" and "Y" with a +/−10.0 mm positioning capability with respect to a plate conveyor. Pipettes can accommodate a flowing wash station and a refilling reagent trough. The pipettes can accommodate 384-well plates, as well as 96-well plates. Pipettes can be a piezo device or a solenoid described herein or known in the art or developed in the future. The liquid level for both aspirating and dispensing can be monitored by placing a sensor on or near the tip of the liquid handler, such as an electrical sensor. For example, the capacitive sensor described in U.S. Pat. No. 5,365,783 (Zweifel) can be used, as well as other suitable sensors known in the art. Such methods can also be applied to other liquid handling devices described herein.

In one embodiment, the screening sample distribution apparatus includes or is designed with a stacker magazine having a capacity of about 50 standard multiwell plates. Bi-directional stacking with lidded or unlidded plates is desirable. The stacker magazine typically may accommodate either standard height multiwell plates or deep well multiwell plates in a given stack, and multiwell plate types will typically not be mixed in a stack. Further, the screening sample distribution apparatus may include or is designed with a bi-directional plate delidder and relidder. The lidder removes and replaces plate lids at a rate of about 5 to 11 plates per minute in one direction. The lidder can store approximately 60 lids. Preferably, a modified lid is used to enable robotic manipulation and separation from the multiwell plate.

Methods of Reformatting

Using the present apparatus, a master plate may be distributed into one or more daughter plates or substrates, for example. The master plate may be aspirated from one or more of the liquid handlers in the sample distribution apparatus. Daughter plates may be positioned under the pipettors. If the replicate volume is large, e.g. volume× replicate number is greater than the tip volume, then multiple aspirations from the master are required. Additionally, it is often faster to bring in four masters and then four daughters (one for each master) and repeat this process until each master is replicated completely. The master may also be 384-well plates and the replicates 96-well plates. In this case, the only difference is that the master must travel under all four pipettors 240 to access each quadrant.

In another embodiment, the master may be an 864-well plate and have nine daughters produced. In another example of an application of the apparatus 200, multiple master plates may be positioned under separate pipettors or heads 240 to be pooled into a single daughter. Each pipettor may dispense to a single daughter. This may be in the same wells or separate wells of a 384-well plate or greater density well plate. Pooling may also consist of more than four masters being combined into a single daughter; this may require the daughter to be sequestered while new masters were aspirated from.

In another example, the sample distribution apparatus can dispense reagents necessary for performing a screen. A sample distribution apparatus can rapidly, accurately and reproducibly dispense solutions in an addressable well in predetermined volumes. The pipette arrays are typically positioned over the desired wells with an X, Y positioner. A suitable X, Y positioner preferably, permits the array to be positioned over wells having a density greater than the density of pipetting tips. This exploits the narrow size of the pipettors to allow the sample distribution apparatus to be used for multiwell plates of different and greater well densities.

Figure 7:
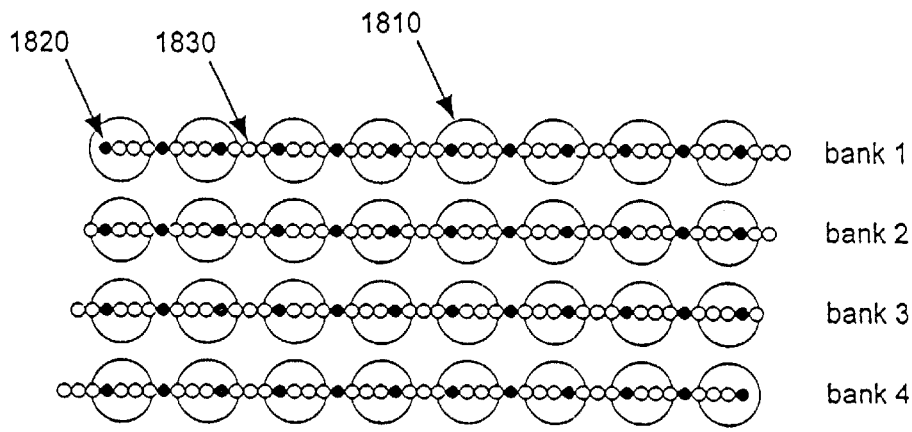
FIG. 7 shows different well densities in relation to different tip positions of a pipette array.
Figure 7:
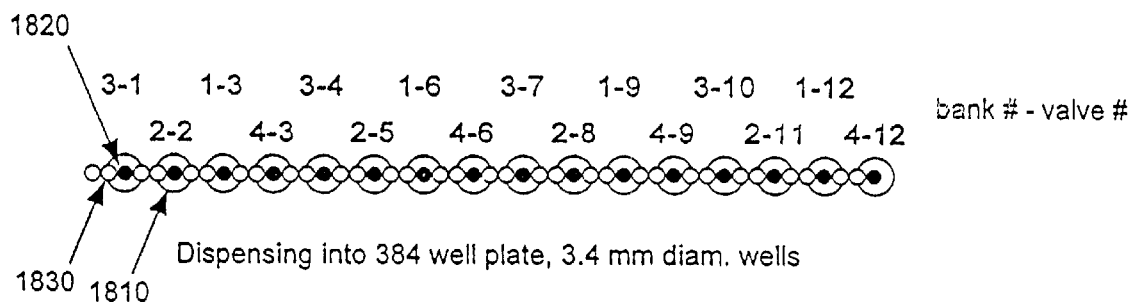
Figure 7:
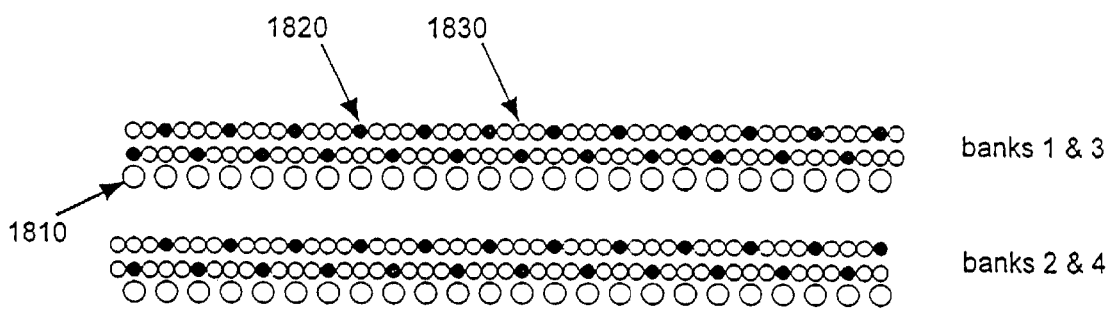

FIG. 7 shows different well densities in relation to different tip positions of a pipette array. A well 1810 is addressed by a possible tip 1820 (filled circles). Also shown are tip positions 1830 (open circles) that may or may not address a well depending on the well density. Each bank shown is an array. The increased spatial density of the pipette and the increased two dimensional density of the target multiwell plate require substantial positioning accuracy. The positioning accuracy tolerance is typically about 200 microns or less, and preferably about 50 microns or less in order to ensure that the proper position in the wells for dispensation can be achieved. This feature enables the rapid distribution of samples into 2-dimensional arrays of varying densities.

Publications

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A chemical solution distribution system for distributing chemical solutions to a plurality of multiwell plates having N wells with I subsets of M wells, I being an integer and greater than one, the system comprising:
    a plurality of liquid handlers, each said liquid handler including:
        a head capable of moving in a Z-direction, said head having M pipettes; and
        a table configured to engage one of said plurality of multiwell plates and movable in an X-Y plane relative to Z, said table capable of moving to at least I different positions,
    wherein at each of said at least I different positions, said M pipettes of said head are aligned with a different one of said I subsets of M wells of said one of said plurality of multiwell plates, and with the proviso that M is about 864 or less.

2. The chemical solution distribution system of claim 1, wherein said system has I liquid handlers.

3. The chemical solution distribution system of claim 1, wherein each of said plurality of said liquid handlers further includes a wash station below said head, wherein said head is capable of moving said M pipettes into contact with solution in said wash station.

4. The chemical solution distribution system of claim 2, said system further including a computational unit to reformat from a first density to a second higher density multiwell plate.

5. The chemical solution distribution system of claim 1, said system further comprising at least one stacker, said stacker capable of storing said plurality of multiwell plates.

6. The chemical solution distribution system of claim 1, said system further including a conveyor belt, said conveyor belt capable of moving at least one of said plurality of multiwell plates between said plurality of said liquid handlers and at least one stacker.

7. The chemical solution distribution system of claim 5, wherein each of said plurality of multiwell plates has a lid, said system further including a delidder, said delidder capable of removing and replacing a lid on each of said plurality of multiwell plates and said conveyor belt further capable of moving said at least one of said plurality of multiwell plates between said plurality of said liquid handlers, said at least one stacker, and said delidder.

8. A chemical solution distribution system of claim 1, wherein M is equal to 96, N is equal to 384, and there are four liquid handlers.

9. The chemical solution distribution system of claim 1, where M is equal to 96.

10. The chemical solution distribution system of claim 1, where M is equal to 96 and N is equal to one of 384 or 864.

11. A chemical solution distribution system for distributing chemical solutions between at least one first multiwell plate having N wells with I subsets of M wells, I being an integer and greater than one and at least one solid substrate or at least one second multiwell plate having M sites or wells, the system comprising:

a plurality of liquid handlers, each liquid handling station including:
  a head capable of moving in a Z-direction, said head having M pipettes; and
  a table configured to engage one of said at least one first multiwell plate having N wells or said at least one second multiwell plate having M wells or said solid substrate and movable in an X-Y plane relative to Z, said table capable of moving to at least I different positions,
wherein at least at I different positions, said M pipettes of said head are aligned with a different one of the I subsets of M wells of the at least one multiwell plate having N wells or at least at one position said M pipettes of said head are aligned with said M wells of said at least one solid substrate or at least one second multiwell plate having M sites or wells, and with the proviso that M is about 864 or less.

12. The chemical solution distribution system of claim 11, wherein said table is movable to I plus one positions.

13. The chemical solution distribution system of claim 12, wherein M is equal to 96.

14. The chemical solution distribution system of claim 13, wherein N is equal to one of 384 or 864.

15. The chemical solution distribution system of claim 13, wherein there are I liquid handlers.

16. A method of distributing chemical solutions between a plurality of plates having N wells with I subsets of M wells, I being an integer and greater than one, said method comprising the steps of:
  aligning a subset of M wells of a first one of said plurality of plates with M pipettes of a first pipette station;
  lowering said M pipettes of said first pipette station to engage said subset of M wells and aspirating solution from M wells into said M pipettes and dispensing solution from said M pipettes into a first set of M wells;
  aligning a subset of M wells of a second one of the plurality of plates with M pipettes of a second pipette station; and
  lowering said M pipettes of said second pipette station to engage said subset of M wells of said second one of the plurality of plates and one of aspirating solution from M wells into said M pipettes and dispensing solution from said M pipettes into a second set of M wells, and with the proviso that M is about 864 or less.

17. The method of claim 16, wherein said samples are chemicals and said plurality of multiwell plates are used to store test chemicals.

18. The method of claim 17, wherein said chemicals comprise polynucleotides.

19. The method of claim 17, further comprising the step of providing a different solution to wash stations of the first liquid handler and said second liquid handler.

20. The method of claim 16, further comprising the steps of:
  aligning a subset of M wells of a third one of said plurality of plates with M pipettes of a third pipette station;
  lowering said M pipettes of said third pipette station to engage the subset of M wells of said third one of said plurality of plates and one of aspirating solution from M wells into said M pipettes and dispensing solution from said M pipettes into a third set of M wells;
  aligning a subset of M wells of a fourth one of said plurality of plates with M pipettes of a fourth pipette station; and
  lowering said M pipettes of said fourth pipette station to engage the subset of M wells of said fourth one of said plurality of plates and one of aspirating solution from M wells into said M pipettes and dispensing solution from said M pipettes into a fourth set of M wells.

21. A method of distributing chemical solutions to a first plate having N wells with I subsets of M wells, I being an integer and greater than one and at least one second plate with about N/I wells, the method comprising the steps of:
  aligning a first subset of N/I wells of said first plate with M pipettes of a first pipette station;
  lowering said M pipettes of said first pipette station to engage said first subset of N/I wells and aspirating solution from said N/I wells into said M pipettes and dispensing solution from said M pipettes into a subset of M wells;
  aligning a second set of N/I wells a second plate with M pipettes of a second pipette station; and
  lowering said M pipettes of said second pipette station to engage said second set of N/I wells of said second plate and aspirating solution from said N/I wells of said second plate into said M pipettes and dispensing solution from said M pipettes into a second subset of M wells and with the proviso that M is about 864 or less.

22. The method of claim 21, further comprising the steps of:
  aligning a third set of N/I wells of one of said plurality of plates with M pipettes of a third pipette station;
  lowering said M pipettes of said third pipette station to engage said third set of N/I wells and aspirating solution from M wells into said M pipettes and dispensing solution from said M pipettes into a third set of M wells;
  aligning a fourth subset of N/I wells of one of said plurality of plates with M pipettes of a fourth pipette station; and
  lowering said M pipettes of said fourth pipette station to engage said fourth set of N/I wells of one of said plurality of plates and aspirating solution from M wells into said M pipettes and dispensing solution from said M pipettes into a fourth set of M wells.

23. The method of claim 22, further comprising the step of providing a different solution to wash stations of said first liquid handler, said second liquid handler, said third liquid handler, and said fourth liquid handler.

24. The method of claim 23, wherein M is equal to 96.

25. The method of claim 24, wherein N is equal to one of 384 or 864.

26. A chemical solution distribution system for distributing chemical solutions into multiwell plates having at least 384 wells, the system comprising:
  a) at least one liquid handler comprising 48 or more, but less than 384, tips, said tips having a dynamic range of liquid dispensation of 100 to 2000 nanoliters, and
  b) an orthogonal positioner, said liquid handler comprising a tip dispensing matrix with about 96 or more tips, being capable of moving said at least one multiwell plate with an X-Y location accuracy of at least ±0.09 mm in X and Y.

27. The device of claim 26, wherein said liquid handler comprises a tip dispensing matrix with about 96 or more tips.

28. The device of claim 27, wherein said tip dispensing matrix comprises no more than 96 tips.

29. A test chemicals distribution system for distributing test chemicals to a plurality of multiwell plates used to store chemical libraries having N wells with I subsets of M wells, I being an integer and greater than one, the system comprising:

a plurality of liquid handlers containing test chemicals, each said liquid handler including:

a head capable of moving in a Z-direction, said head having M pipettes; and a table configured to engage one of said plurality of multiwell plates and movable in an X-Y plane relative to Z, said table capable of moving to at least I different positions, wherein at each of said at least I different positions, said M pipettes of said head are aligned with a different one of said I subsets of M wells of said one of said plurality of multiwell plates, and with the proviso that M is about 864 or less.

30. A chemical solution distribution system for distributing chemical solutions comprising polynucleotides to a plurality of multiwell plates having N wells with I subsets of M wells, I being an integer and greater than one, the system comprising:

a plurality of liquid handlers containing chemical solutions comprising polynucleotides, each said liquid handler including:

a head capable of moving in a Z-direction, said head having M pipettes; and a table configured to engage one of said plurality of multiwell plates and movable in an X-Y plane relative to Z, said table capable of moving to at least I different positions, wherein at each of said at least I different positions, said M pipettes of said head are aligned with a different one of said I subsets of M wells of said one of said plurality of multiwell plates, and with the proviso that M is about 864 or less.

* * * * *